US006873414B2

(12) United States Patent
Schüth et al.

(10) Patent No.: US 6,873,414 B2
(45) Date of Patent: Mar. 29, 2005

(54) METHOD AND APPARATUS FOR THE COMBINATORIAL PREPARATION AND TESTING OF MATERIAL LIBRARIES BY PHOTOACOUSTIC ANALYTICAL METHODS

(75) Inventors: Ferdi Schüth, Mulheim (DE); Armin Brenner, Spiesheim (DE); Stephan Andreas Schunk, Heidelberg (DE)

(73) Assignee: hte Aktiengesellschaft, Hiedelberg (DE)

( * ) Notice: Subject to any disclaimer, the term of this patent is extended or adjusted under 35 U.S.C. 154(b) by 410 days.

(21) Appl. No.: 09/773,534

(22) Filed: Feb. 2, 2001

(65) Prior Publication Data

US 2002/0017617 A1 Feb. 14, 2002

(30) Foreign Application Priority Data

Feb. 4, 2000 (DE) .......................................... 100 04 816

(51) Int. Cl.[7] .............................................. G01N 21/61
(52) U.S. Cl. ...................................................... 356/432
(58) Field of Search ............................. 356/432; 436/37

(56) References Cited

U.S. PATENT DOCUMENTS

| | | | | |
|---|---|---|---|---|
| 4,099,923 A | | 7/1978 | Milberger .................. 23/254 R |
| 4,492,862 A | * | 1/1985 | Grynberg et al. ........... 250/255 |
| 5,151,474 A | | 9/1992 | Lange et al. .................. 526/60 |
| 5,959,297 A | | 9/1999 | Weinberg et al. ........... 250/288 |
| 6,087,181 A | * | 7/2000 | Cong .......................... 356/432 |
| 6,495,105 B1 | * | 12/2002 | Yamada et al. ............... 436/37 |

FOREIGN PATENT DOCUMENTS

| | | |
|---|---|---|
| EP | 0 749 011 | 12/1996 |
| WO | 97/32208 | 9/1997 |
| WO | 98/15813 | 4/1998 |
| WO | 98/15969 | 4/1998 |
| WO | 99/19724 | 4/1999 |

OTHER PUBLICATIONS

WO 99/41005 Abstract only.
Derwent Abstract of DE 198 05 719 Feb. 12, 1998.
A. Bohren et al., "Optical parametric oscillator based difference frequency laser source for photoacoustic trace gas spectroscopy in the 3 $\mu$m mid–IR range.", Infrared Physics & Technology 38, (1997) pp. 423–435.
Arnold Holzwarth et al., "Detection of Catalytic Activity in Combinatorial Libraries of Heterogenous Catalysts by IR Thermography.", Angew. Chem. Int. Ed. (1998) vol. 37, No. 19, pp. 2644–2647.
Manfred T. Reetz et al., "Time–Resolved IR–Thermographic Detection and Screening of Enantioselectivity in Catalytic Reactions.", Angew. Chem. Int. Ed. (1998) vol. 37, No. 19, pp. 2647–2650.
Philippe Repond et al., "Photoacoustic spectroscopy on trace gases with continuously tunable $CO_2$ laser.", Applied Optics, vol. 35, No. 21, Jul. 20, 1996, pp. 4065–4085.
Markus W. Sigrist, "Laser photoacoustics for gas analysis and materials testing.", Optical engineering, vol. 34, No. 7, 1916–1922.

* cited by examiner

Primary Examiner—Richard A. Rosenberger
(74) Attorney, Agent, or Firm—Jones Day

(57) ABSTRACT

Method for determining useful properties of individual building blocks of a material library including a substrate having at least two individual building blocks in at least two sections separated from one another, which method includes: (ii) introducing at least one starting material into at least two sections of a substrate of a material library which are separated from one another, in order to carry out a chemical or physical or chemical and physical reaction of the starting material in the at least two substrate sections separated from another, in each case in the presence of the corresponding building block, obtaining in each case an effluent comprising at least one reaction product and/or starting material and, (iii) analysing the effluent obtained in the reaction according to (ii) comprising at least one reaction product and/or starting material; the effluent being analysed by recording and analysing at least one photoacoustic signal.

17 Claims, 4 Drawing Sheets

METHOD AND APPARATUS FOR THE COMBINATORIAL PREPARATION AND TESTING OF MATERIAL LIBRARIES BY PHOTOACOUSTIC ANALYTICAL METHODS

BACKGROUND OF THE INVENTION

The present invention relates to a method for the combinatorial preparation of material libraries and testing of the same by photoacoustic analytical methods and an apparatus for carrying out this process.

Photoacoustic methods are known for the analysis of substances in gases, liquids and solids. The physical effect of photoacoustics is based on the absorption of light energy by a molecule and the subsequent detection of the heat released by relaxation of the molecule, which can be measured as a pressure wave by microphonic measuring systems in a measuring instrument. The broad applicability of the method is based on the great number of molecular de-excitation processes which lead to a heating of the analyte and thus to a change in volume. The technical set-up for measuring the photoacoustic effect is, compared with other analytical methods, relatively simple and is associated with moderate equipment costs. The essential constituents of a measuring apparatus for determining photoacoustic signals comprise an excitation light source, a measuring device for recording the photoacoustic signals, preferably a microphone, and a data recording and analysis unit for analysing the signals produced, and if appropriate for controlling the light source and/or the measuring device.

With respect to the relevant prior art, reference is made to P. Remond, Applied Optics 1996, 35, No. 21, pp. 4065 to 4083 and to A. Bohren, Infrared Physics & Technology 1997, 38, pp. 423 to 435.

Using the photoacoustic effect, with a suitable measuring system and the currently known methods, even traces of substances can be detected down to the ppm range in gases and liquids within a few minutes of measuring time. Photoacoustics is thus one of the most sensitive and rapid optical analytical methods (cf. M. W. Sigrist, Optical Engineering, 1995, 34, No. 7, pp. 1916 to 1922).

For some time, combinatorial methods have been the centre of attention for research and development in the material research sector. By means of these combinatorial methods, as great a number as possible of different or identical chemical compounds are continuously being prepared and thus a material library established, which compounds are then studied for useful properties using suitable methods. In addition to magnetic, electronic, electromagnetic, optical, electrooptical and electromechanical properties, etc., catalytic properties of such materials prepared by combinatorial or highly parallel methods are also the centre of attention. In this respect, reference is made to WO 99/41005 and the prior art cited therein. This publication relates to arrays of heterogeneous catalysts and/or their precursors, made up of a body which has preferably parallel continuous channels and in which at least n channels contain n different heterogeneous catalysts and/or their precursors, where n has the value 2, preferably 10, particularly preferably 100, in particular 1000, especially 10,000. In addition, the publication relates to a process for preparing such arrays and a process for determining the activity, selectivity and/or long-term stability of catalysts in such an array.

U.S. Pat. No. 4,099,923 describes a substantially automated test unit for testing heterogeneous catalysts. The system described there consists of a tube-bundle reactor in which the same starting-material flow flows through each of the tubes. In the effluent of the tubes, the resultant products are passed via a multiway valve to a gas chromatograph and are there analysed for target products. The unit described there offers only a relatively small degree of parallelization, a system having 6 parallel tubes being given as an example. Obviously, in principle, a greater number of tubes is conceivable. However, the fact remains a problem that all gases in the described embodiment are passed for analysis via a multiway valve and thus sequential analysis of the samples takes place. If a higher degree of parallelization is wanted, this can be achieved by connecting further analytical instruments. However, this is associated with undesirably high capital costs.

WO 98/15969 and U.S. Pat. No. 5,959,297 describe the analysis of material libraries using translatable capillaries which take samples at defined places and pass these to an analytical instrument. In this case also, the same restrictions apply as for U.S. Pat. No. 4,099,923, this is a sequential processing of a finite number of samples in which the degree of parallelization can only be achieved by increasing the analytical capacity. For tests of particularly large numbers of building blocks from material libraries, this method is also not very suitable.

Relatively large material libraries can be simply investigated by analysing the heat formed in the reaction. In this case according to WO 97/32208 and WO 98/15813, using a thermosensitive camera, an entire material library can be studied for its useful properties. The disadvantage of the method is essentially that the thermosensitive camera reflects only the degree of activity of the catalysts via the heat being released. For a number of reactions this information is sufficient (total oxidations, complete hydrogenations, etc.) (see, inter alia, Holzwarth, A., Schmidt, H. W., Maier, W. F. Angewandte Chemie, 1998, 110, 19, 2788–2791; Reetz, M. T., Becker, M. H., Holzwarth, A., Angewandte Chemie, 1998, 110, 19, 2792–2795); in the case of other reactions, especially partial oxidations of hydrocarbons, to evaluate catalytic properties of a building block of a material library, information about the activity alone is not sufficient, since the selectivity of the building block in such types of reactions generally plays a greater role than the activity.

WO 99/19724 describes an optical method (REMPI) which makes it possible, by combining ionizing excitation of gases present in the effluent of a reactor with detection of the ionized molecules by one or more electrodes situated at the reactor outlet close to the ion production point, to detect selectively in parallel certain products in the effluent of a reactor or reactor array. Via this method, both the activity and the selectivity of the catalysts can be tested under conditions close to actual use. However, the method has a disadvantage due to the physical method of analysis. It is simple for a small number of organic molecules to produce characteristic ions which can be detected simply. However, with the majority of organic molecules, in each case very similar ion fragments are formed by the action of laser light under the conditions typical of this method. This prevents unambiguous detection of these molecules and unambiguous assignment of activity and selectivity parameters to the individual active compositions. A further disadvantage of the method is that when the analytical electrodes are operated for a relatively long period coking or polymer formation and thus destruction of the electrodes by the product gas must be expected.

SUMMARY OF THE INVENTION

In view of the information described above, an object underlying the present invention was to provide a method and an apparatus for determining useful properties of individual building blocks of a material library, which method does not have the disadvantages of the methods previously used in the analysis of such material libraries and, furthermore, provides information simply and quickly on useful properties, preferably catalytic properties, and in this case in particular activity and selectivity, of building blocks of a material library.

These and other objects are achieved by a method for determining useful properties of individual building blocks of a material library comprising a substrate having at least two individual building blocks in at least two sections separated from one another, which method comprises:

(ii) introducing at least one starting material into at least two sections of a substrate of a material library which are separated from one another, in order to carry out a chemical or physical or chemical and physical reaction of the starting material in the at least two substrate sections separated from another, in each case in the presence of the corresponding building block, obtaining in each case an effluent comprising at least one reaction product and/or starting material and (iii) analysing the effluent obtained in the reaction according to (ii) comprising at least one reaction product and/or starting material characterized in that the effluent is analysed by recording and analysing at least one photoacoustic signal;

and by a method which, in addition to the above mentioned steps, comprises the following further prior step (i):

(i) establishing the material library comprising a substrate having at least two individual building blocks in at least two different substrate sections separated from one another;

and furthermore by an apparatus for carrying out the above-described methods, which comprises:

(1) means for holding at least two individual building blocks comprising a substrate having at least two different sections separated from one another, (2) means for introducing at least one starting material, (3) equipment for detecting and analysing photoacoustic signals.

DETAILED DESCRIPTION OF PREFERRED EMBODIMENTS

Figure 1:
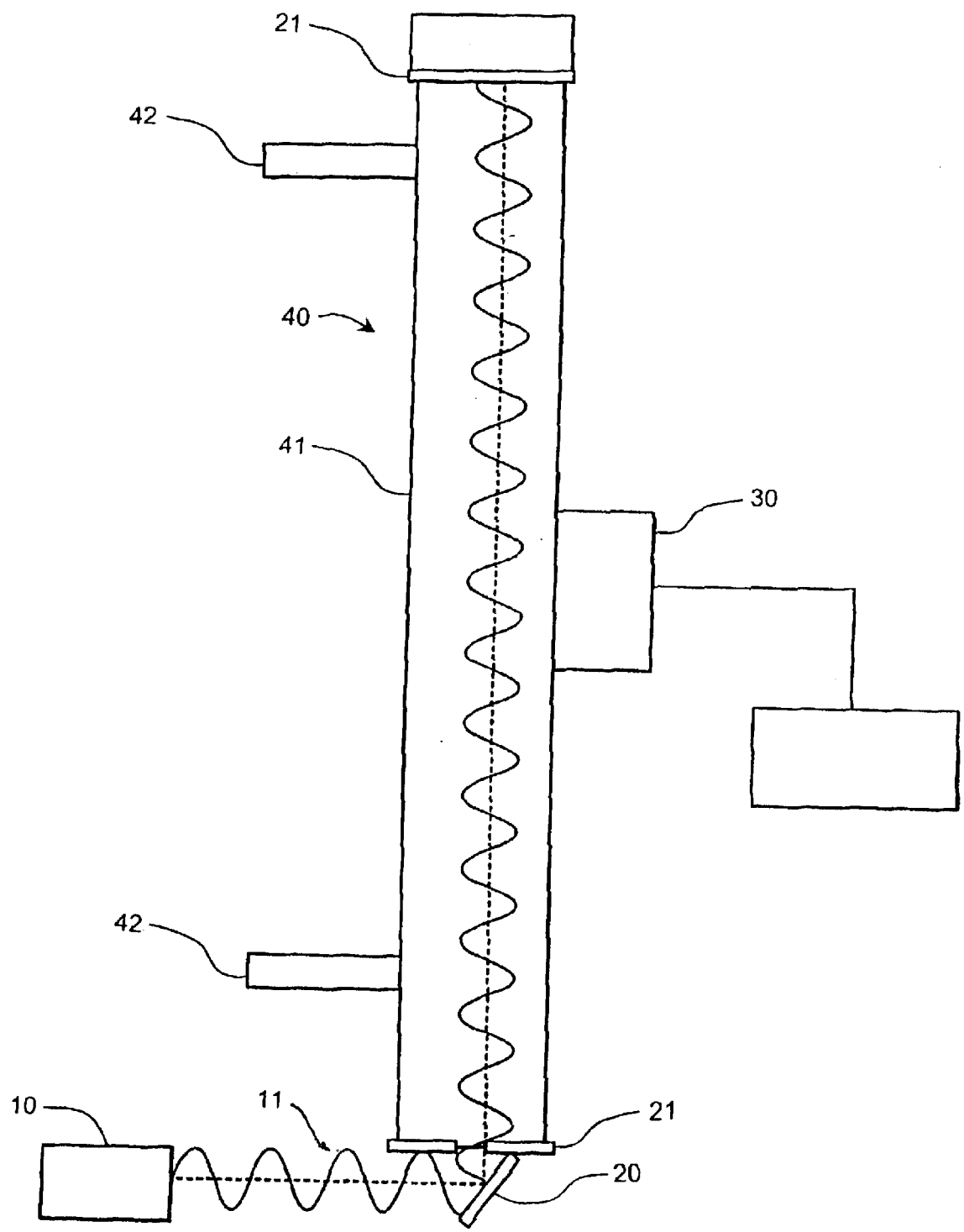
FIG. 1 corresponds to the outline set-up of the measuring system for recording a photoacoustic signal with the aid of a resonant or non-resonant measuring cuvette.

The term "material library" used for the purposes of the present invention denotes an arrangement of at least two, preferably up to 10, further preferably up to 100, in particular up to 1000, and further preferably up to 100,000, building blocks which are situated in at least two substrate sections which are separated from one another.

The term "building block" denotes an individual defined unit which is situated in the individual substrate sections which are separated from one another and which can consist of one or more components.

The term "substrate" comprises in principle all devices having a rigid or semi-rigid surface which can be either flat or can have recesses or bore holes or channels. The substrate must be suitable for physically separating from one another the at least two individual building blocks in the at least two different sections separated from one another. Preferably, the substrate comprises channels which are continuous in parallel and further preferably represents a tube-bundle reactor or heat exchanger. The geometric arrangement of the individual sections to one another can be chosen freely in this case. For example, the sections can be arranged in the manner of a row (virtually one-dimensionally), a chessboard pattern (virtually two-dimensionally) or in circle form (circular). In the case of a substrate having parallel continuous channels, preferably tube-bundle reactor or heat exchanger having a multiplicity of tubes which are parallel to one another, the arrangement of the tubes becomes clear when considering a cross-sectional area perpendicular to the longitudinal axis: a surface results in which the individual tube cross sections reflect the different areas spaced from one another. The sections or tubes can, for example for tubes having a circular cross section, also be present in a dense packing so that different numbers of sections are arranged offset to one another.

The term substrate describes a three-dimensional object which has a multiplicity (at least 2) of "sections". Preferably, these sections are tubes, but they can also represent individual sections which are physically separated from one another of a flat or recessed substrate, for example in the form of a spot plate. Preferably, the sections are formed as channels. The channels thus connect two surface areas of the substrate and run through the substrate. Preferably, the channels are essentially, preferably completely, parallel to one another. The substrate can in this case be made of one or more materials and can be solid or hollow. It can have any suitable geometric shape. Preferably, it has two surfaces which are parallel to each other in which one of the channel openings is situated in each case. The channels preferably run in this case perpendicular to these surfaces. One example of a substrate of this type is a parallelepiped or cylinder in which the channels run between two parallel surfaces. However, a multiplicity of similar geometries is also conceivable.

The term "channel" describes a connection passing through the substrate between two openings present on the body surface, which connection permits, for example, the passage of a fluid through the body. The channel can in this case have a desired geometry. It can have a cross-sectional area which is changeable over the length of the channel or preferably a constant channel cross-sectional area. The channel cross section can have, for example, an oval, round or polygonal periphery having straight or bent connections between the corners of the polygon. Preference is given to a round or equilateral polygonal cross section. Preferably, all channels in the body have the same geometry (cross section and length) and run in parallel to one another.

The terms "tube-bundle reactor" and "heat exchanger" describe collected parallel arrangements of a multiplicity of channels in the form of tubes, in which case the tubes can have any desired cross section. The tubes are arranged in a fixed spatial relationship to one another, and are preferably spatially separated from one another and preferably are enclosed by a shell which contains all tubes. By this means, for example a heating or cooling medium can be passed through the shell, so that all tubes are heated or cooled evenly.

The term "block of a solid material" describes a substrate of a solid material (which in turn can be made of one or more starting materials) which contains the channels, for example in the form of bore holes. The geometry of the channels (bore holes) can be in this case, as described above for the channels in general, selected freely. The channels (bore holes) need not be introduced by drilling, but can also be left open, for example, during shaping of the solid body/block, for instance by extrusion of an organic and/or inorganic moulding composition (for example by an appropriate die geometry during extrusion). In contrast to the tube-bundle reactors or heat exchangers, the space in the body between the channels in the block is always filled by the solid material. Preferably, the block is made of one or more metals.

The term "predefined" denotes that, for example, a number of different or identical building blocks, for example catalysts or catalyst precursors, is introduced into, for example, a tube-bundle reactor or heat exchanger, in such a manner that the assignment of the individual building blocks, for example catalysts or precursors, to the individual tubes is recorded and can later be accessed, for example when determining useful properties, for example activity, selectivity and/or long-term stability, of the individual building blocks, for example catalysts, in order to make possible unambiguous assignment of defined analytical values to defined building blocks. Preferably the building blocks are prepared and distributed under computer control onto the different regions, in which case the individual composition of a building block and the position of the section in the substrate, for example tube-bundle reactor, into which the catalyst or catalyst precursor is introduced, is stored in a computer and can later be accessed. The term "predefined" thus serves for differentiation from a chance or random distribution of the individual building blocks among the substrate sections.

The term "photoacoustic signal" comprises sound signals which are generated owing to the absorption of light by the reaction product or reaction products and/or the starting material or the starting materials (analyte), with the light source, preferably a laser, being modulated with time. The modulation can be performed, for example, by chopping a continuous wave light signal or by pulsing the light source.

The respective photoacoustic signals are assigned to the individual building blocks/sections either via acoustic transit time measurements or by assigning a sound signal to a scanning motion of the light source and/or the microphone.

The term "analyte" denotes the reaction product or reaction products and/or the starting material or starting materials which are analysed by means of the photoacoustic signal.

The present invention thus relates in particular to a method of the type in question here, which is characterized in that the substrate is a tube-bundle reactor or heat exchanger and the regions are channels, preferably tubes, or the substrate is a block of a solid material which has regions, preferably channels.

In addition, the at least two individual building blocks preferably have useful properties and further preferably are heterogeneous catalysts and/or their precursors, further preferably are inorganic heterogeneous catalysts and/or their precursors and in particular are solid catalysts or supported catalysts and/or their precursors. They are present here preferably in each case as catalyst bed, tube-wall coating or auxiliary support coating. In the context of the present invention the individual building blocks can be identical or different from one another. If they are different from one another, the reaction conditions selected during the reaction can be identical or different, if the building blocks are identical, preferably the reaction conditions are different in the individual regions.

Obviously, the concept described therein and which is described hereunder predominantly for heterogeneous catalyst systems may also be applied to other building blocks, for example homogeneous catalyst systems, in particular organometallic systems, organic substances, for example pharmacological active compounds, polymers, composite materials, in particular those made of polymers and inorganic materials. In principle, the inventive process is applicable to all areas of the technique in which formulations, that is to say compositions having more than one constituent, are produced and are studied for their useful properties. Fields of application outside material research are, for example, drug formulations, formulations of food supplements, feeds and cosmetics.

Step (i)

The material libraries or the individual building blocks present therein can be prepared as described in general below, where, with respect to further details, WO 99/19724, WO 96/11878 and WO 99/41005 are incorporated by reference. The following methods may be mentioned individually:

Methods for applying thin films, for example electron beam vaporization, sputtering, thermal vaporization, plasma vaporization, molecular beam epitaxy, deposition from the gas phase, deposition using a laser which can be modulated; coprecipitation and impregnation; impregnation of suitable support materials, for example porous silicon dioxide or aluminium oxide, which are introduced as above in each case into the substrate sections. The active component(s) can be applied by applying solutions, suspensions or pastes which in each case comprise the active component(s) or one or more suitable compounds thereof. There are no restrictions with respect to the supports which can be used, with reference being able to be made here in particular to porous and monolithic supports.

In addition, it is also possible to prepare material libraries which comprise homogeneous building blocks, for example homogeneous catalysts. For this purpose, for example, organometallic or inorganometallic compounds and/or any desired complex molecules, for example enzymes, are used, with the use of a suitable device, for example a suitable pipette having a plurality of channels, in order to introduce the building blocks into the corresponding sections separated from one another.

In particular, the material libraries investigated according to the invention may be established by the following procedures which are described by way of example on the basis of the inorganic heterogeneous catalysts and/or their precursors which are also preferably used in the context of the present invention. See WO 99/41005 for further details of procedures (a) to (f) described below.

Procedure (a) comprises the following steps:

a1) preparation of solutions, emulsions and/or dispersions of elements and/or compounds of elements of the elements present in the catalyst and/or catalyst precursor, and if appropriate of dispersions of inorganic support materials, a2) if appropriate introduction of adhesion promoters, binders, viscosity regulators, pH-controlling agents and/or solid inorganic supports into the solutions, emulsions and/or dispersions, a3) simultaneous or sequential coating of the substrate channels with the solutions, emulsions and/or dispersions, in which case a predefined amount of the solutions, emulsions and/or dispersions is introduced into each channel in order to obtain a predefined composition, and a4) if appropriate heating the coated body, in the presence or absence of inert gases or reactive gases, to a temperature in the range from 20 to 1500° C. to dry and if appropriate sinter or calcine the catalysts and/or catalyst precursors.

Procedure (b) comprises the following steps:

b1) preparation of solutions, emulsions and/or dispersions of elements and/or compounds of elements of the elements present in the catalyst and/or catalyst precursor, and if appropriate of dispersions of inorganic support materials, b2) if appropriate introduction of adhesion promoters, binders, viscosity regulators, pH-controlling agents and/or solid inorganic supports into the solutions, emulsions and/or dispersions, b3) simultaneous or sequential coating of the catalyst supports present in the substrate channels with the solutions, emulsions and/or dispersions, in which case a predefined amount of the solutions, emulsions and/or dispersions is introduced into each channel in order to obtain a predefined composition on the catalyst supports, and b4) if appropriate heating the substrate together with the coated catalyst supports in the channels, in the presence or absence of inert gases or reactive gases, to a temperature in the range from 20 to 1500° C. to dry and if appropriate sinter or calcine the catalysts and/or catalyst precursors.

Procedure (c) comprises the following steps:

c1) preparation of solutions, emulsions and/or dispersions of elements and/or compounds of elements of the chemical elements present in the catalyst and/or catalyst precursor, and if appropriate of dispersions of inorganic support materials, c2) mixing predefined amounts of the solutions, emulsions and/or dispersions and if appropriate precipitation aids in one or more reaction vessels operated in parallel, c3) if appropriate introduction of adhesion promoters, binders, viscosity regulators, pH-controlling agents and/or solid inorganic supports into the resultant mixture(s), c4) coating one or more predefined substrate channels with the mixture or a plurality of mixtures, c5) repetition of steps c2) to c4) for other substrate channels until the channels are coated with the catalyst composition and/or catalyst precursor composition predefined in each case, c6) if appropriate heating the coated body, in the presence or absence of inert gases or reactive gases, to a temperature in the range from 20 to 1500° C. to dry and if appropriate sinter or calcine the catalysts and/or catalyst precursors.

Preferably the procedure comprises the following steps:

c1) preparation of solutions of compounds of elements of the chemical elements except for oxygen present in the catalyst, and if appropriate of dispersions of inorganic support materials, c2) mixing predefined amounts of the solutions or dispersions and if appropriate precipitation aids in one or more reaction vessels operated in parallel with precipitation of the chemical elements present in the catalyst, c3) if appropriate introduction of adhesion promoters, binders, viscosity regulators, pH-controlling agents and/or solid inorganic supports into the resultant suspension, c4) coating one or more predefined tubes of the tube-bundle reactor or heat exchanger with the suspension, c5) repetition of steps c2) to c4) for different tubes of the tube-bundle reactor or heat exchanger until the tubes are coated with the catalyst compositions predefined in each case, c6) heating the coated tube-bundle reactor or heat exchanger, in the presence or absence of inert gases or reactive gases, to a temperature in the range from 20 to 1500° C. to dry and if appropriate sinter or calcine the catalysts.

Procedure (d) comprises the following steps:

d1) preparation of solutions, emulsions and/or dispersions of elements and/or compounds of elements of the chemical elements present in the catalyst and/or catalyst precursor, and if appropriate of dispersions of inorganic support materials, d2) mixing predefined amounts of the solutions, emulsions and/or dispersions and if appropriate precipitation aids in one or more reaction vessels operated in parallel, d3) if appropriate introduction of adhesion promoters, binders, viscosity regulators, pH-controlling agents and/or solid inorganic supports into the resultant mixture(s), d4) coating catalyst supports present in one or more predefined substrate channels with the mixture or one or more of the mixtures, d5) repetition of steps d2) to d4) for other (that is to say generally the still uncoated) catalyst supports in the substrate channels until the (preferably all) catalyst supports present in the substrate channels are coated with the catalyst composition and/or catalyst precursor composition (generally differing from one another) predefined in each case, d6) if appropriate heating the substrate together with the coated catalyst supports in the channels, in the presence or absence of inert gases or reactive gases, to a temperature in the range from 20 to 1500° C. to dry and if appropriate sinter or calcine the catalysts and/or catalyst precursors.

The adhesiveness of the channels (for example the inner surface of the tubes) of the substrate or of the catalyst supports can be increased prior to the coating by chemical, physical or mechanical pretreatment of the inner walls of the channels (for example inner tubes) or of the catalyst supports or by applying an adhesive layer; this applies in particular to procedures (a) and (c) and, respectively, (b) and (d).

Procedure (e) comprises the following steps:

e1) preparation of differing heterogeneous catalysts and/or their precursors in the form of solid catalysts having a predefined composition, e2) charging in each case one or more predefined substrate channels which are secured to prevent the heterogeneous catalysts from falling out with in each case one or more of the heterogeneous catalysts and/or their precursors having a predefined composition, e3) if appropriate heating the body containing the heterogeneous catalysts and/or their precursors in the channels, in the presence or absence of inert gases or reactive gases, to a temperature in the range from 20 to 1500° C. to dry and if appropriate sinter or calcine the catalysts and/or catalyst precursors.

Procedure (f) comprises the following steps:

f1) coating and if appropriate heating predefined catalyst supports to produce predefined supported catalysts outside the body in the manner defined above in methods (b) and (d), f2) introduction of the supported catalysts into predefined substrate channels, f3) if appropriate heating the packed substrate, in the presence or absence of inert gases or reactive gases, to a temperature in the range from 20 to 1500° C. to dry and if appropriate sinter or calcine the catalysts.

Preferably in this case the outer shape of the supported catalysts corresponds to the shape of the channel interior in the body at least essentially, preferably approximately or completely.

The procedures outlined above are suitable for producing a multiplicity of catalyst systems, as are described, for example, in G. Ertl, H. Knözinger, J. Weitkamp, editors, "Handbook of Heterogeneous Catalysis ", Wiley—VCH, Weinheim, 1997.

See the section "Production of the inorganic heterogeneous catalyst array" of WO 99/41005 for further details regarding the establishment of a material library in accordance with (i) of the inventive method. In this section, the establishment of a material library (there termed "array") is described in detail with reference to the establishment of a material library of inorganic heterogeneous catalysts. The content of this section of WO 99/41005 is, moreover, incorporated by reference completely in the context of the present application. Obviously, the concept described there may also be applied to other building blocks, for example homogeneous catalyst systems, in particular organometallic systems, organic substances, for example pharmacological active compounds, polymers, composite materials, in particular those of polymers and inorganic materials. In principle, the inventive method is applicable to all fields of the art where formulations, that is to say compositions having more than one constituent, are prepared and analysed for their useful properties. Fields of application outside material research are, for example, drug formulations, formulations of food and food supplements, feeds and cosmetics.

Therefore, the present invention is not restricted to determining the useful properties of defined catalyst materials and catalyst compositions. The mixtures mentioned above can be prepared in this case in parallel or sequentially and generally in automated form, for example using an automated pipetter or pipetting robot, by means of an ink-jet method, as is described, for example, in U.S. Pat. No. 5,449,754, or by means of automated sputtering or electrolysis methods.

In addition to procedures (a) to (f) described above, it is obviously also possible to prepare differing heterogeneous catalysts in the form of solid catalysts or supported catalysts having a predefined composition by known methods, for example combinatorial methods and to charge in each case one or more predefined sections, preferably tubes of a tube-bundle reactor or heat exchanger or tubes or auxiliary supports introduced into these, with each of these prefabricated heterogeneous catalysts.

Step (ii)

The chemical or physical or chemical and physical reaction of the starting material in the at least two substrate sections separated from one another, with an effluent comprising at least one reaction product being obtained, according to step (ii) can be carried out as follows.

Firstly, if necessary, the catalyst can be activated in the substrate. This can be carried out by thermal treatment under inert or reactive gases or by other physical and/or chemical treatments. Then, the substrate is brought to a desired reaction temperature and thereafter a fluid starting material which can be an individual compound or a mixture of two or more compounds is passed through or along the substrate through one, a plurality or all of the sections, preferably channels, of the substrate.

The fluid starting material, consisting of one or more reactants, is generally liquid, or preferably gaseous. Preferably, oxidation catalysts, for example, are tested by parallel or sequential impingement of individual, a plurality or all sections, preferably tubes, of a coated tube-bundle reactor, with a gas mixture of one or more saturated, unsaturated or polyunsaturated organic starting materials. Those which may be mentioned in this case are, for example, hydrocarbons, alcohols, aldehydes etc., and oxygen-containing gases, for example air, $O_2$, $N_2O$, NO, $NO_2$, $O_3$ and/or, for example, hydrogen. Furthermore, an inert gas, for example nitrogen or a noble gas, can also be present. The reactions are generally carried out at temperatures of 20 to 1200° C., preferably at 50 to 800° C., and in particular at 80 to 600° C., in which case by means of a suitable device the parallel or sequential separate removal of the respective gas streams of individual, a plurality or all sections is ensured.

The resultant effluent comprising at least one reaction product is then either collected from individual or a plurality of sections of the substrate and preferably analysed separately, sequentially or preferably in parallel and the analytical results are analysed.

A plurality of reactions, each interrupted by a flushing step with a flushing gas, can also be carried out and analysed sequentially at identical or different temperatures. Obviously, identical reactions are also possible at different temperatures.

Preferably, at the start of the method, the collected effluent of the entire library is analysed in order to establish whether a reaction has occurred at all. In this manner, groups of building blocks can be very rapidly analysed as to whether they have any useful properties, for example catalytic properties. Obviously, after carrying out this "coarse screening", again individual groups of building blocks can be analysed together in order to establish again which groups of building blocks have catalytic properties, if a plurality of such groups of building blocks are present in the material library.

The invention permits the automated production and catalytic testing for mass screening of, for example, heterogeneous catalysts for chemical reactions, in particular for reactions in the gas phase, very particularly for partial oxidations of hydrocarbons in the gas phase with molecular oxygen (gas-phase oxidations).

For the study, suitable reactions or conversions are described in G. Ertl, H. Knözinger, J. Weitkamp, editors, "Handbook of Heterogeneous Catalysis", Wiley —VCH, Weinheim, 1997. Examples of suitable reactions are primarily listed in this reference in volumes 4 and 5 under the numbers 1, 2, 3 and 4.

Examples of suitable reactions are the decomposition of nitrogen oxides, the synthesis of ammonia, ammonia oxidation, oxidation of hydrogen sulphide to sulphur, oxidation of sulphur dioxide, direct synthesis of methylchlorosilanes, oil refining, oxidative coupling of methane, methanol synthesis, hydrogenation of carbon monoxide and carbon dioxide, conversion of methanol to hydrocarbons, catalytic reforming, catalytic cracking and hydrocracking, carbon gasification and liquefaction, fuel cells, heterogeneous photocatalysis, synthesis of ethers, in particular MTBE and TAME, isomerizations, alkylations, aromatizations, dehydrogenations, hydrogenations, hydroformylations, selective or partial oxidations, aminations, halogenations, nucleophilic aromatic substitutions, addition and elimination reactions, dimerizations, oligomerizations and metathesis, polymerizations, enantioselective catalysis and biocatalytic reactions and for material testing, and in this case in particular for determining interactions between two or more components at surfaces or substrates, in particular in the case of composite materials.

The removal of the respective effluents comprising at least one reaction product and/or the starting material, which is preferably obtained separately from the respective sections, is preferably performed via a device which is connected gas-tightly to the respective sections. Those which may be mentioned are in particular sampling by means of suitable flow guidance, for example, valve switches and mobile capillary systems (sniffing apparatus). The individual effluents of the individual sections, a plurality of sections or all sections can be removed separately in this case and then analysed separately via a valve switch.

The for example computer-controlled mechanically movable "sniffing apparatus" comprises a sniffing line for the effluent to be sampled, which line is positioned essentially automatically on, in or above the outlet of the respective section and then samples the effluent. Details with respect to the arrangement of such a "sniffing apparatus" may also be taken from WO 99/41005 already repeatedly cited above.

However, preferably, analysis is performed in the "free" gas space. The effluent of the entire substrate is analysed with light in this case and the resultant photoacoustic signal is assigned to one or more sections/building blocks of the substrate.

Step (iii)

The effluent obtained in the reaction in accordance with step (ii) is analysed according to the invention by recording and analysing at least one photoacoustic signal. In principle the elemental requirements of a photoacoustic system which can be used according to the invention are restricted to the following important features:

1. light source exciting molecular vibrations, rotations, electronic excitation states, chemical reactions or combinations of these processes of chemical compounds which are situated in the reaction product and/or the starting material;
2. at least one measuring device for recording the photoacoustic signals, for example pressure gradient transducers such as microphones, pressure transducers such as barometers, or combinations of these, for example ultrasonic transducers.
3. at least one data recording and analysis unit for analysing the photoacoustic signals generated, and
4. if appropriate a collecting device, preferably a measuring cuvette, in which the effluent is present in the gaseous, liquid or solid state, but in the simplest case operations can also be carried out in the free gas space.

The excitation light source used can be any monochromatic light source. Use is made, in particular, of laser light, preferably laser light of various wavelengths, further preferably modulatable laser light, in particular laser light of a predefinable, modulatable CW laser or CW laser provided with an iris system, with wavelengths in the medium infrared range, that is to say in the range from 1 to 20 $\Box m^{-1}$, being preferred. There are no restrictions with regard to the laser used, provided that this operates at a wavelength which corresponds to characteristic molecular bands. In principle gas lasers, dye lasers, solid-state lasers and semiconductor lasers can be used. The use of laser light has the advantage that this is a highly coherent, monochromatic light source of high power which permits very precise "sampling" of individual frequencies and thus characteristic molecular vibrations. Although in principle it is sufficient to use a laser light source which matches the compounds or their absorption to be expected in the effluent, it is useful to use one or more tuneable lasers in order to be able to carry out absorption experiments on a plurality of different substances. This mode of operation makes it possible not only to determine the conversion rate (activity) and the selectivity of the catalyst used, but also it is useful, especially with complex product mixtures in the effluent, to have the possibility of being able to irradiate in different absorption bands of a molecule and thus to free the sought-after product or products and/or starting materials from by-products which have some absorption bands overlapping those of the desired product/starting material.

In particular, the following laser systems are suitable for use in the present method:

Solid-state lasers, in particular those which operate in the wavelength range from 430 to 2000 nm, for example Nd-YAG lasers which are preferably equipped with optical parametric oscillators; tuneable gas lasers, for example $CO_2$ and CO lasers, HeNe lasers; dye lasers, in particular those which emit in the medium infrared region of preferably 1 to 20 $\Box m^{-1}$; semiconductor lasers.

It is necessary to modulate the light, especially the laser light. This can be carried out in a manner known to those skilled in the art, in which case, the following methods/systems in particular may be mentioned:

Chopper systems, for example mechanical irises, optical parametric oscillators; suitable filter/polarizing filter circuits; suitable rotating and/or vibrating mirror systems or electrical power modulation of the laser power. In addition to these methods of amplitude modulation, however, the frequency can also be modulated, by "travelling" in and out of the absorption wavelength.

In the context of the present invention, the laser light can be beamed in parallel or perpendicular or at any angle to the effluent.

For further details, see Applied Optics 1996, 35, pp. 4065–4085, Optical Engineering, 1995, 34, pp. 1916–1922 and Infrared Physics & Technology, 1997, 38, pp. 423–435, the contents of which are completely incorporated by reference into the context of the present invention.

The photoacoustic signal is detected according to the invention by one or more microphones which can convert the incoming sound signal(s) into electrical signals.

Generally, the following procedure can be followed here:
1. Recording the signal in a cuvette or the free effluent using a microphone measuring device;
2. Filtering the signal via a suitable amplification technique, for example lock-in technique;
3. Analysing the signal via analogue and/or digital analysing electronics;
4. If appropriate, calibration can be carried out using a reference signal which is generated in a reference cuvette and/or the free effluent and/or a reference section and/or a microphone reference measuring device.

According to the invention a procedure is followed here so that in each case one microphone is arranged per section, preferably in each case one microphone is arranged for more than one section, and in particular only one microphone is arranged per substrate (=for all sections).

The effluent can be collected and analysed in a measuring cuvette. A resonant or non-resonant cuvette can be employed here. Preferably, the useful property of a building block is analysed and determined in one or more of the sections of the substrate in the free effluent via sequential scanning or transit time measurement methods.

The data produced are then analysed by a data recording and analysis unit.

The present invention will now be described again in more detail using preferred embodiments with reference to the drawings.

Recording and Analysis of the Photoacoustic Signals Using at Least One Measuring Cuvette (FIG. 1)

In the effluent of a reactor (40) comprising a plurality of sections which each comprise one catalyst, are arranged one or more measuring cuvettes (41) such that each measuring cuvette (41) is assigned to a catalyst by means of a suitable flow guide, for example a valve switch or sniffing device. This can be achieved, for example, by using a tube-bundle reactor in the tubes of which are present different or identical catalysts. The effluents can be passed into the measuring cuvettes (41) by capillaries adapted to the individual tubes. The individual capillaries can be constructed here in such a manner that a laser beam (11) is beamed in by the laser (10) through a hole at one of the reflecting ends of the measuring cuvette (41). This beam is reflected at the other reflecting end (21) of the measuring cuvette (41), the reflecting ends (21) of the cuvette (41) preferably being fixed at the Brewster angle. The reflecting coating achieves an internal reflection in the cuvette (41) which causes an amplification of the signal. Long-path cells can also be used to increase the sensitivity. The cuvette (41) can be constructed in this case in such a manner that, with a suitable pulse frequency of the excitation laser (10), a resonant sound wave is formed, as a result of which the signal intensity is considerably intensified. However, it is possible to operate in a non-resonant state. Both when a resonant sound wave and when a non-resonant sound wave is present, the microphone (30) is advantageously arranged at the side cuvette wall in the centre of the beam path between the two mirrors (20, 21), but other embodiments, for example a non-central arrangement of the microphone (30), are also possible here.

By using cuvettes having reflecting ends (mirrors (21)), an internal measurement signal magnification takes place in such a manner that extremely small, i.e. down into the ppb region, concentrations of target molecules can be determined at great dilution. A further advantage of such a cuvette arrangement is the very exact reproducible amount of gas which flows through the cuvette through gas inlets and outlets (42), as a result of which simple testing, for example of the flow velocity and the analyte concentration in the cuvette, is possible. Obviously, it is possible to establish the flow velocity or the throughput of effluent precisely via the gas inlets.

As a result it is possible, in particular, to work under defined flow rates and to determine the concentration of the products in the effluent exactly, which is extremely important for precise estimation of the selectivity of the catalyst used.

Figure 2:
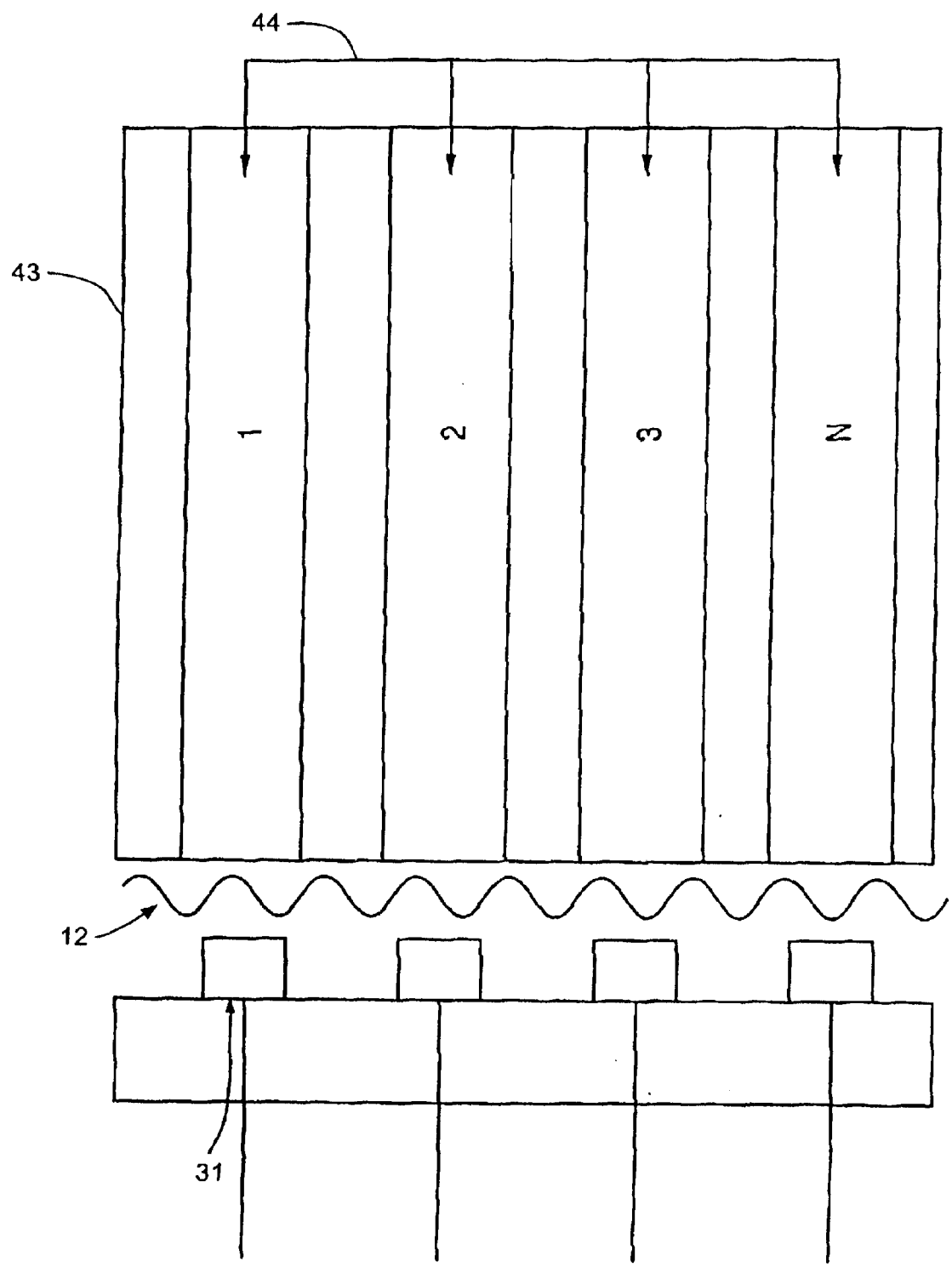
FIG. 2 shows an emobodiment of the present invention, in which one microphone is arranged per section of the substrate and the analysis of the effluent takes place in the free gas space.

Embodiment Having in Each Case One Detector/Microphone Above the Outlet of the Individual Reaction Channels (FIG. 2)

In this embodiment, one microphone (31) is arranged in a reactor (43) having n gas inlets (44) having a number of n reaction channels containing catalysts (1, 2, 3, ..., n). The reaction channels are arranged in this case in such a manner that the light beam (12) of the laser is guided along or past the effluent of all channels via suitable mirror arrangements. If in the effluent of one of the channels a reaction product then appears which adsorbs at the respective wavelength of the laser, then here, directly at the reaction channel, the expansion of the gas caused by the heat is detected by the microphone (31). The reaction channels, the arrangement of the microphones and the electronic circuitry are designed in such a manner here that unambiguous assignation of the sound pulses to the individual channels is possible from the differences in transit times of the sound waves.

The photoacoustic signal is assigned to a respective section/building block in this case via measurement of the transit time difference. A trigger signal which is switched via the light source can be used for the analysis here.

Figure 3:
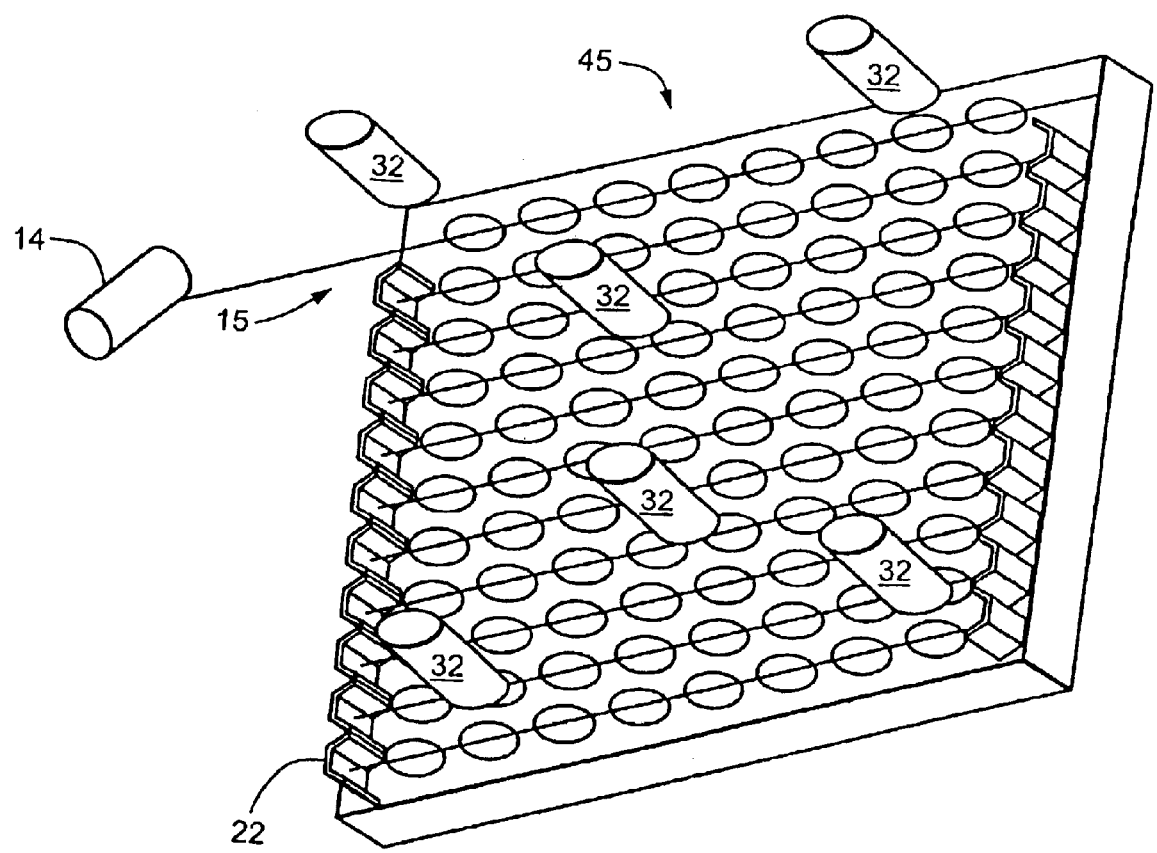
FIG. 3 shows an embodiment of the present invention in which the number of microphones is less than the number of building blocks or sections.

Arrangement of a Number of Microphones Around and/or Below and/or Above a Number of Reaction Channels Through which Reaction Gas Flows, the Number of Microphones Being Less than the Number of Catalysts (FIG. 3)

In this case around and/or below and/or above an arrangement of catalysts (45) which can be accommodated in individual tubes or are situated on a plate through which or over which flow passes, are fixed a defined number of microphones (32) around and/or below and/or above a laser arrangement (14), in which case the microphones (32) occupy certain positions which are well defined with respect to the positions of the catalysts in the arrangement (45) or are arranged in such a way that they can be moved above the substrate by means of a suitable motor system. The laser light (15) is guided over the arrangement (45) by a suitable mirror arrangement (22). If the expected product emerges above one of the catalysts, owing to the photoacoustic effect, the gas is heated above this point. The resultant sound pressure is then detected by the various microphones (32) which are arranged above the arrangement (45). However, the time point at which the signal is detected by the microphones (32) is always differentiated by the transit time of the sound wave. By the transit time difference, with suitable analysis, the section at which the target molecules enter the gas stream can be established. Thus determination of the activity and the selectivity of a building block within the substrate and determination of the position of the sound source, that is of the respective section/building block, is possible.

In addition to the planar, 2-dimensional substrate arrangement described, other substrate arrangements are also possible. In addition, the individual sections can also be analysed sequentially, for example by scanning with the light source and/or the microphone.

Figure 4:
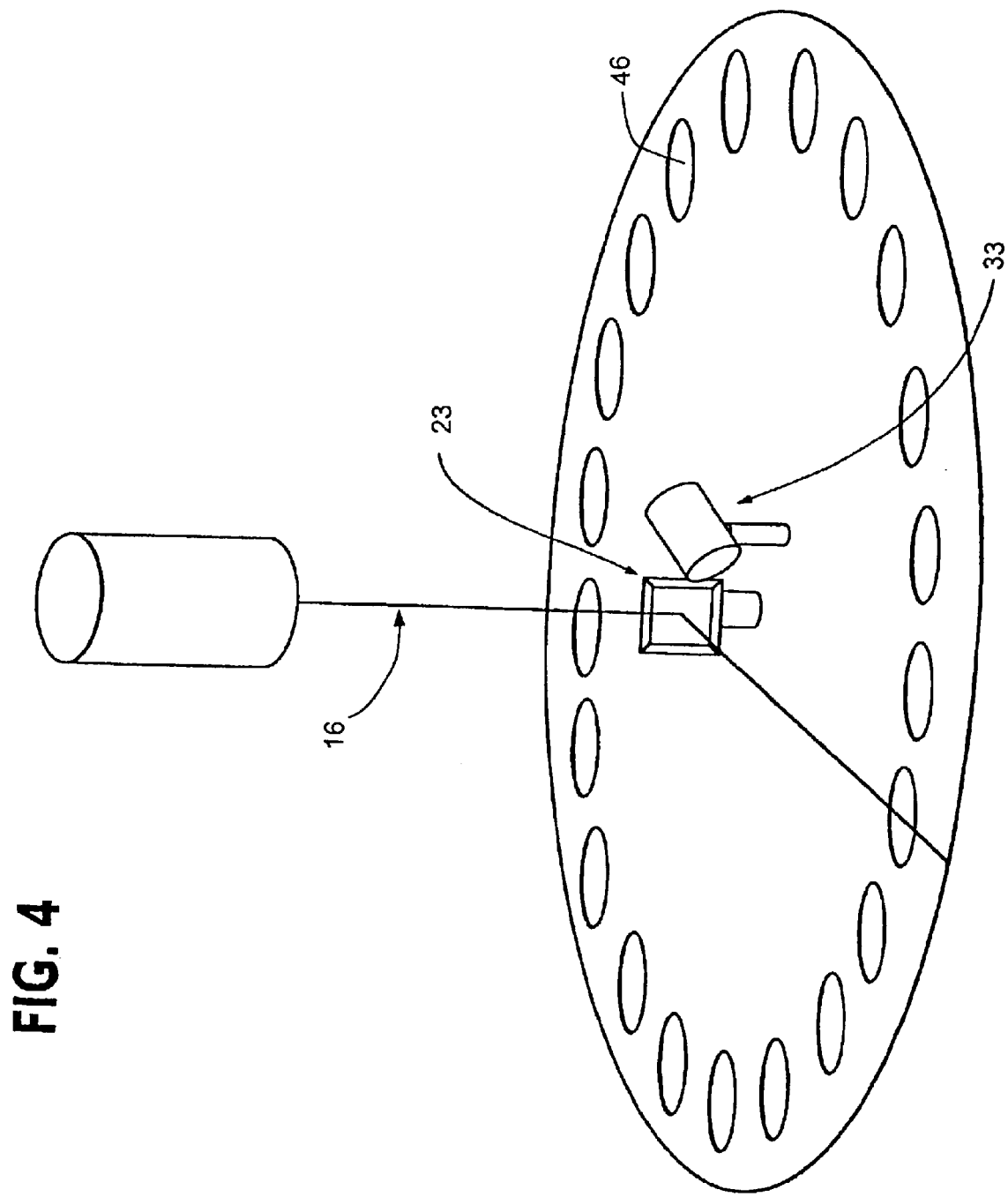
FIG. 4 shows an embodiment of the present invention in which sequential excitation and analysis of the photoacoustic signal takes place.

Central Arrangement of Light Source and Microphone in a Circular Substrate for the Highly Integrated Sequential Analysis of the Effluents of the Individual Sections (FIG. 4)

In this embodiment, the effluents of the individual sections (46) are arranged in a circle around a rotatable mirror (23), next to or on which are situated one or more preferably rotatable microphones (33). The laser beam (16) is coupled to the mirror (23) at any angle, preferably orthogonally to the circular arrangement of the sections (46). The laser light (16) is deflected via the mirror (22) onto the effluent of the individual channels. The photoacoustic signal is detected by the microphone/microphones (33) which is/are installed so as to be able to be moved and/or is/are fixed. Via the arrangement described, a highly integrated sequential analysis of the individual sections/building blocks (46) is possible with a minimum number of microphones (33).

As is implied above, in the context of the present method it is possible relatively simply and in particular rapidly to analyse a great number of building blocks, in particular catalysts, with respect to their useful properties. In this case in the case of catalysts their relative activity and selectivity occupy the foreground, with the catalyst activity being able to be determined in proportion to the intensity of the signal and the selectivity being able to be determined via the different absorption wavelengths.

In addition, the present invention also relates to an apparatus for carrying out the method outlined above which comprises:

(4) means for holding at least two individual building blocks comprising a substrate having at least two different sections separated from one another, (5) means for introducing at least one starting material, (6) equipment for detecting and analysing photoacoustic signals.

Regarding particularly preferred embodiments of this apparatus reference is made here to the descriptions above with respect to the inventive method.

In addition the present invention also relates to the use of the method described herein and the apparatus described herein for determining useful properties of building blocks of a material library, in particular for determining the activity, selectivity and/or long-term stability of building blocks which have catalytic properties.

The inventive method is carried out, in particular, in such a manner that at least one, preferably all, of the steps (i) to (iii), as described in detail above, are carried out in parallel in each case, as a result of which the method in question here enables in particularly rapid manner the determination of useful properties of building blocks of a material library. Automated equipment, for example robots, may also be used in the inventive method.

The priority document here, German Patent Application No. 10004816.1 filed Feb. 4, 2000, is hereby incorporated by reference.

What is claimed is:

1. A method for use with a material library, the material library including a substrate with separate sections, each section having a building block, the method comprising:

introducing a starting material into each section to react the starting material in the presence of the respective building block to yield an effluent;

causing the effluent of each section to emit a photoacoustic signal;

detecting the signals using a microphone;

distinguishing the signal emitted by each effluent from the signals emitted by the other effluents based on differences in transit time required for each signal to reach the microphone; and analyzing each effluent based on the signal from the effluent.

2. The method of claim 1 wherein the detecting step includes detecting the signals using also another microphone, and the distinguishing step includes distinguishing the signal emitted by each effluent from the signals emitted by the other effluents based on differences in transit time for each signal to reach each microphone.

3. The method of claim 2 wherein, in the detecting step, the total number of signals detected is greater than the total number of microphones used.

4. The method of claim 1 wherein the causing step includes irradiating each effluent with time modulated laser light.

5. The method of claim 1 wherein the causing step includes irradiating each effluent with pulsed or chopped light.

6. The method of claim 1 wherein, during the detecting step, the microphone is above the sections.

7. The method of claim 1 wherein the reaction is selected from the group consisting of decomposition of nitrogen oxides, synthesis of ammonia, ammonia oxidation, oxidation of hydrogen sulphide to sulphur, oxidation of sulphur dioxide, direct synthesis of methylchlorosilanes, oil refining, oxidative coupling of methane, methanol synthesis, hydrogenation of carbon monoxide and carbon dioxide, conversion of methanol to hydrocarbons, catalytic reforming, catalytic cracking and hydrocracking, carbon gasification and liquefaction, heterogeneous photocatalysis, synthesis of ethers, synthesis of MTBE, synthesis of TAME, isomerizations, alkylations, aromatizations; dehydrogenations, hydrogenations, hydroformylations, selective oxidations, partial oxidations, aminations, halogenations, nucleophilic aromatic substitutions, addition and elimination reactions, dimerizations, oligomerizations and metathesis, polymerizations, enantioselective catalysis, biocatalytic reactions, and combinations thereof.

8. The method of claim 1 further comprising determining the activity, selectivity, and/or long-term stability of building blocks that have catalytic properties based on the results of the analyzing step.

9. The method of claim 1 wherein each building block is a catalyst.

10. The method of claim 1 wherein each building block is a heterogeneous catalyst and/or a precursor of a heterogeneous catalyst.

11. The method of claim 10 wherein the heterogeneous catalyst is inorganic.

12. The method of claim 1 wherein each building block is in the form of a tube-wall coating.

13. The method of claim 1 wherein each building block is lube form of an auxiliary support coating.

14. An apparatus comprising:

a material library having a substrate that includes separate sections, each section having a building block;

means for introducing a starting material into each section to react in the presence of the respective building block to yield an effluent;

a light source configured to cause the effluent of each section to emit a photoacoustic signal;

a microphone configured to detect the signals;

means for distinguishing the signal emitted by each effluent from the signals emitted by the other effluents based on differences in transit time for each signal to reach the microphone; and means for analyzing each effluent based on the signal from the effluent.

15. The apparatus of claim 14, further comprising another microphone configured to detect the signals, wherein the means for distinguishing includes means for distinguishing the signal emitted by each effluent from the signals emitted by the other effluents based on differences in transit time for each signal to reach each microphone.

16. The apparatus of claim 15 wherein the number of sections, and thus the number of signals to be detected by the microphones, exceeds the number of microphones.

17. The apparatus of claim 14 wherein the light source is a time modulated laser light source.

* * * * *

UNITED STATES PATENT AND TRADEMARK OFFICE
CERTIFICATE OF CORRECTION

PATENT NO. : 6,873,414 B2
DATED : March 29, 2005
INVENTOR(S) : Schuth et al.

It is certified that error appears in the above-identified patent and that said Letters Patent is hereby corrected as shown below:

Title page,
Item [73], Assignee, "hte Aktiengesellschaft" should read -- hte Aktiengesellschaft the high throughput experimentation company --

Column 16,
Lines 37-38, "The method of claim 1 wherein each building block in the form of an auxillary support coating." should read -- The method of claim 1 wherein each building block in the form of an auxillary support coating. --

Signed and Sealed this

Thirty-first Day of May, 2005

JON W. DUDAS
*Director of the United States Patent and Trademark Office*